United States Patent [19]

Ludwig et al.

[11] Patent Number: 5,320,724
[45] Date of Patent: Jun. 14, 1994

[54] METHOD OF MONITORING CONSTITUENTS IN PLATING BATHS

[75] Inventors: Frank A. Ludwig, Rancho Palos Verdes; Bruce M. Eliash; Nguyet H. Phan, both of Los Angeles; Vilambi N. R. K. Reddy, Lakewood, all of Calif.

[73] Assignee: Hughes Aircraft Company, Los Angeles, Calif.

[21] Appl. No.: 977,344

[22] Filed: Nov. 17, 1992

[51] Int. Cl.⁵ .............................................. G01N 27/26
[52] U.S. Cl. .................................. 204/153.1; 204/402; 204/412; 204/434; 204/435
[58] Field of Search ............ 204/402, 412, 434, 153.1, 204/DIG. 8, DIG. 9, 435; 205/81, 101, 102, 103, 104, 105

[56] References Cited

U.S. PATENT DOCUMENTS 4,631,116 12/1986 Ludwig ................................. 204/434

*Primary Examiner*—John Niebling
*Assistant Examiner*—Bruce F. Bell
*Attorney, Agent, or Firm*—M. E. Lachman; M. W. Sales; W. K. Denson-Low

[57] ABSTRACT

A method of monitoring a plating bath which combines ac and dc voltammetry to accurately measure major and trace constituent concentrations. The method involves applying both ac and dc voltammetric signals to a pretreated electrode in contact with the plating bath solution, measuring the ac and dc response current spectra, and comparing the resultant spectra to determine which provides maximum spectral detail for monitoring particular constituents with minimum interference from other constituents. Then, the ac and dc response current spectra are each used to monitor the particular constituents for which each provides the best accuracy. The method complements and is easily integrated with known voltammetric techniques and equipment.

8 Claims, 1 Drawing Sheet

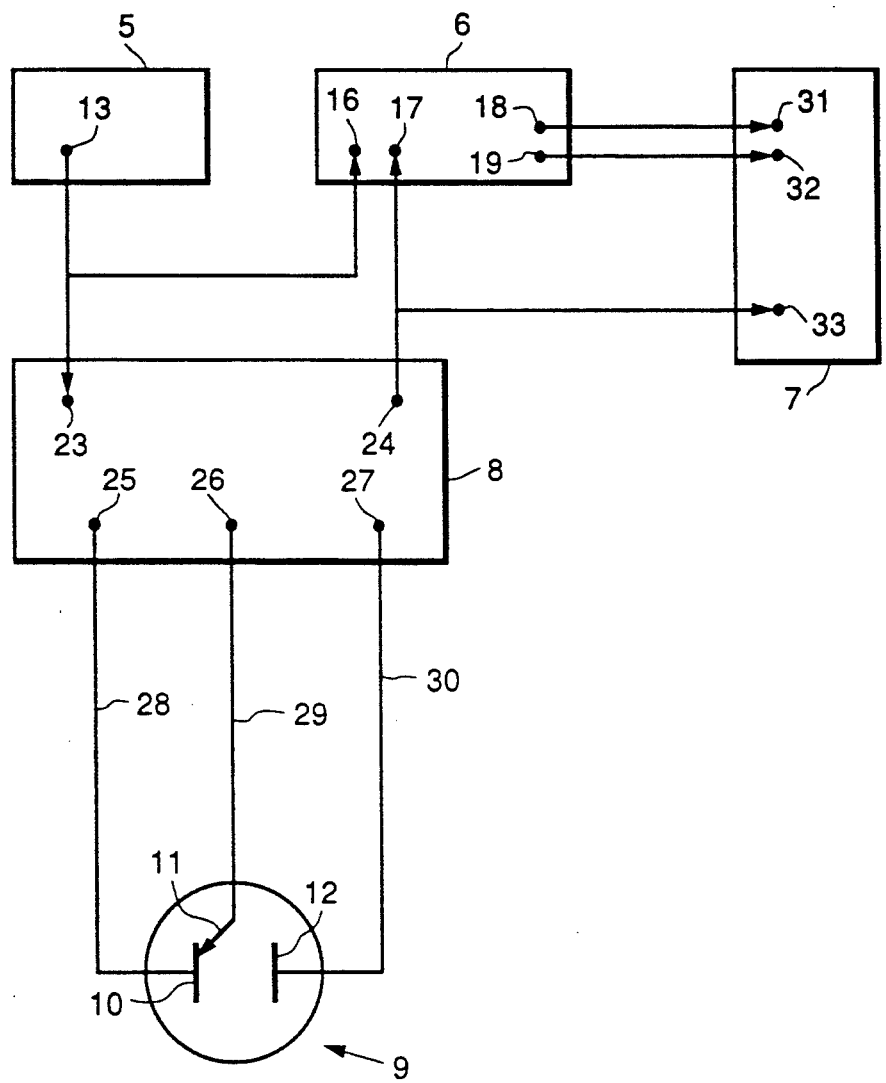

METHOD OF MONITORING CONSTITUENTS IN PLATING BATHS

This invention was made with support from the United States Government provided under Contract Number DAAB07-85-C-A047 awarded by the Department of the Army. The United States Government has certain rights in this invention.

BACKGROUND OF THE INVENTION

1. Field of the Invention

The present invention relates generally to plating baths and methods for monitoring the constituents contained therein. More particularly, the present invention relates to a method for systematically applying both ac and dc voltammetric signals to a plating bath solution in order to obtain ac and dc spectra which accurately indicate constituent concentration levels. The method can be used to maintain desired major and trace constituent concentrations in order to ensure optimal plating bath performance.

2. Description of Related Art

A typical plating bath solution is comprised of a combination of several different electrochemical constituents. The specific constituents vary depending upon the type of plating bath, but in general can be broadly divided into what are commonly known as major constituents and trace, or minor, constituents. The major constituents are those electrochemical constituents which make up about 2 to 50 percent of the total bath weight or volume. Trace constituents, on the other hand, are present in smaller quantities, usually less than one percent of the total volume. For example, in an acid cadmium plating bath, cadmium ions and sulfuric acid are major constituents, and organic addition agents, degradation products and chemical contaminants are typical trace constituents.

The concentration levels of both major and trace constituents are important determinants of the quality of the resultant plating deposit. Trace constituent concentrations influence certain characteristics of the plating deposit, including tensile strength, ductility, solderability, uniformity, brightness and resistance to thermal shock. Monitoring and optimization of trace constituents assumes that the major constituent concentrations within the bath are already properly set and maintained. Should the major constituents fall outside of required concentration ranges, however, the bath may fail to satisfactorily perform its plating function. It is therefore important that both major and trace constituent concentrations be regularly monitored.

Current major constituent monitoring techniques typically involve removing a sample of the electrochemical solution from the plating tank for subsequent wet or instrumental chemical analysis. Typical methods of measuring major constituent content in various types of plating baths are disclosed in K. E. Langford and J. E. Parker, "Analysis of Electroplating and Related Solutions," pages 83–100, 65–68 and 174–180. Wet or instrumental chemical analysis methods such as these usually must be performed by highly skilled personnel. Specialized and costly chemical analysis equipment and supplies are required. Furthermore, the delay between drawing samples and receiving measurement results can be anywhere from several hours to several days. It is thus very tedious and expensive to monitor major constituent concentrations using currently available techniques. Moreover, the slow response time of some wet chemical analysis limits the extent to which a high quality plating bath can be continuously maintained.

Trace constituent monitoring techniques, however, can provide accurate results in real time without wet chemical analysis. The method disclosed in U.S. Pat. No. 4,631,116, assigned to the present assignee, uses ac voltammetry to produce response current spectra which vary as a result of changes in the concentration of various trace constituents. Other techniques, such as polarographic stripping, use dc voltammetric signals to analyze the plating bath. Both ac and dc voltammetric techniques have been found to produce accurate results in real time for trace constituent analysis. However, these techniques have not yet been considered for analyzing major constituents.

Furthermore, a single ac or dc voltammetric technique is unlikely to produce optimal measurement results for all trace constituents in all types of plating baths. In any constituent measurement, it is important that the measurement be selective, that is, substantially unaffected by other constituents in the bath. The measurement should also be very sensitive to the presence of the desired constituent. However, in certain cases, the ac or dc voltammetric signal response to one constituent is susceptible to interference from other constituents, which leads to decreased sensitivity and ambiguous measurement results. For example, the ac technique of U.S. Pat. No. 4,631,116 does not produce completely unambiguous response current spectra for multiple organic addition agents in the acid cadmium bath discussed above.

Under current practice, therefore, no single technique or set of equipment is sufficiently flexible to measure a wide variety of major and trace constituents. Wet or instrumental chemical analysis is typically used for major constituent measurement, and a variety of ac or dc techniques for trace constituent measurement. No integrated measurement system is available which combines the attributes of several measurement techniques. As a result, plating bath users must bear the additional expense of maintaining several sets of equipment for measuring different constituents. Furthermore, there is no efficient strategy for selecting among the various voltammetric techniques available. Users must rely on trial and error to select the most appropriate ac or dc technique for a given application.

As is apparent from the above, there presently is a need for an improved method of monitoring plating bath major and trace constituents which combines and extends the capabilities of existing techniques. The method should provide a systematic strategy for obtaining the most selective and sensitive response spectra for measuring a particular major or trace constituent. Furthermore, the method should be capable of providing the advantages of different voltammetric techniques using a single set of measurement equipment, resulting in a flexible and efficient overall plating bath analysis system.

SUMMARY OF THE INVENTION

In accordance with the present invention, a method is provided for monitoring the concentration of major and trace constituents within a plating bath. The present invention is based upon the discovery that the use of dc voltammetry in conjunction with ac voltammetry can yield accurate measurement results for a wider variety of constituents than heretofore thought possible. By considering both ac and dc current spectra, the method of the present invention provides a systematic strategy for determining the most selective and sensitive analysis technique for specific plating bath constituents.

The method of the present invention involves the steps of applying a pretreatment signal of sufficient amplitude and duration to a working electrode in contact with a plating bath solution containing several constituents; applying an ac voltammetric signal to the pretreated electrode, thereby producing an ac response current; measuring the ac response current spectra at one or more phase angles with respect to the voltammetric signal; applying another pretreatment signal to the electrode; applying a dc voltammetric signal to the pretreated electrode, thereby producing a dc response current; measuring the dc response current spectra; comparing the ac and dc spectra detail to determine which spectra provide maximum selectivity and sensitivity to the concentration levels of particular constituents; using the ac current spectra to monitor the concentration of those particular constituents for which the ac current spectra provide optimal spectral detail; and using the dc current spectra to monitor the concentration of those particular constituents for which the dc current spectra provide optimal spectral detail.

As a feature of the present invention, the method can provide optimal response current spectra for both major and trace constituents and thereby avoid the inefficiency and delay associated with major constituent wet or instrumental chemical analysis techniques. Specialized chemical equipment and analysis personnel are no longer required. The measurement results are available in real time so that the ideal constituent levels, and thereby the quality of the plating bath, can be continuously and efficiently maintained.

In accordance with the present invention, both ac and dc current spectra are obtained for a given plating bath, thereby providing improved measurement capability over either ac or dc techniques in isolation. For example, the method can accurately determine the concentration level of particular organic addition agents in an acid cadmium plating bath using dc voltammetry, and the concentration level of the other agents using ac voltammetry. Certain of the organic agents are more accurately distinguished using dc voltammetry than using ac voltammetry, and vice versa. The method provides similar accuracy improvements for other types of plating baths.

As a further feature of the present invention, the method is easily integrated with known trace constituent measurement methods and equipment, thereby providing an efficient and flexible overall plating bath analysis system suitable for accurately monitoring a wide variety of plating baths and their respective major and trace constituents. Since the present invention can be implemented using voltammetric equipment suitable for trace constituents, only a single set of equipment need be maintained. The method of the present invention thus serves to complement and extend the capabilities of existing voltammetric analysis techniques.

As an additional feature of present invention, optimal signal parameters for monitoring the concentrations of exemplary major and trace constituents within commonly used plating baths are disclosed. Furthermore, the method provides an experimental framework for determining optimal measurement signal parameters for monitoring major constituents in other types of plating baths.

The above-discussed features and attendant advantages of the present invention will become better understood by reference to the following detailed description of the invention and the accompanying drawings.

BRIEF DESCRIPTION OF THE DRAWINGS

FIG. 1 is a schematic representation of a preferred exemplary system for conducting the method of the present invention.

DESCRIPTION OF THE PREFERRED EMBODIMENTS

The present invention uses ac and dc voltammetric signals, generated using a common set of equipment, to provide accurate measurement spectra for both major and trace constituents in a variety of different plating baths. In any given plating bath, certain voltammetric techniques may be more selective and sensitive than others for measuring a given constituent. Instead of applying separate techniques independently, the present method generates both ac and dc spectra for a plating bath. The method then uses the ac and dc spectra to determine the particular constituent concentrations for which each provides the optimal spectral detail and therefore the best selectivity and sensitivity. Some of the dc and ac methods involve interferences from other constituents. In order to maximize selectivity, those methods are chosen which minimize interferences. In some cases, minimization of interferences is provided by dc methods; in others by ac methods.

Although the present description will focus on some exemplary voltammetric techniques, ac voltammetry as disclosed in U.S. Pat. No. 4,631,116 and specific dc voltammetry, it should be noted that the method of the present invention is not limited to these two techniques. The method can be used to combine any ac and dc voltammetric techniques to establish a flexible system for monitoring both major and trace constituents. Furthermore, although the following description applies the method to exemplary chromium and acid cadmium plating baths, the present invention has wide application to many other plating baths and the constituents contained therein.

The schematic diagram of FIG. 1 illustrates a preferred exemplary system for conducting the method of the present invention. This system is used to provide both ac and dc voltammetric signals, and is readily compatible with the equipment of U.S. Pat. No. 4,631,116. The contents of this patent are hereby expressly incorporated by reference. The present method thus extends the capability of trace voltammetric techniques without requiring additional equipment.

In the exemplary system of FIG. 1, the plating bath solution is located within an electrochemical cell 9. The electrochemical cell 9 is preferably part of an in-tank electrochemical sensor submerged within the plating bath. The solution can be drawn through the in-tank sensor by a pump. The potentiostat 8 serves to generate electrode pretreatment signals of appropriate amplitude and duration. The pretreatment signal removes any adsorbed organics or other contaminants from the working electrode 10 which might interfere with ac or dc voltammetric measurements. Alternatively, the pretreatment signal could be supplied by the function or waveform generator 5. Waveform generator 5 provides an output 13 which is a voltammetric signal of appropriate frequency and amplitude. The voltammetric signal is applied to the external input 23 of potentiostat 8 and as a coherent reference to the reference input 16 of a lock-in amplifier 6.

In the case of the ac voltammetric signal, the waveform generator 5 provides a constant amplitude ac signal to the external potentiostat input 23. This constant amplitude ac signal is superimposed on a sweep signal generated within potentiostat 8. Alternatively, the sweep signal could be supplied by a second external waveform generator (not shown). In some cases the voltammetric signal is simply the one generated within potentiostat 8, upon which the ac is superimposed. In other cases the dc signal is a constant voltage dc plating signal followed by a constant voltage dc stripping signal. For ac and dc voltammetric signals, the potentiostat 8 further serves to insure that the voltammetric signal amplitude does not vary as a result of variations in current flow through the electrochemical cell 9.

The voltammetric signal output from potentiostat port 25 is then applied to the working electrode 10, usually a platinum wire, in the electrochemical cell 9 via line 28. The electrochemical cell 9 also contains a counter electrode 12 and a standard calomel or any other convenient reference electrode 11. The reference electrode 11 and counter electrode 12 are connected to potentiostat ports 26, 27 via lines 29, 30, respectively. The electrochemical cell 9 with electrodes 10, 11 and 12 is a sensor design typically used in conjunction with voltammetric techniques. Other sensor designs could also be used. When either the ac or dc voltammetric signal is applied to the working electrode 10, a response current is generated between the working electrode 10 and the counter electrode 12. The response current signal parameters vary depending upon the electrochemical processes occurring at the surface of the working electrode 10. The electrochemical processes are a function of the constituent concentrations, and the response current is therefore responsive to these concentrations.

Both the superposed ac and dc voltammetric signal response currents are passed back through the potentiostat 8. From the potentiostat output 24 the response current is applied to the signal input 17 of lock-in amplifier 6 and to the external sweep input 33 of strip chart recorder 7 or to computerized data acquisition system 7. In the case of the ac voltammetric signal response current, the lock-in amplifier serves to separate out the desired ac response current and resolve the first or second harmonic into in-phase and quadrature components. The dc voltammetric signal, however, need not be resolved into components before being displayed or computer analyzed. Certain filters are used with system 7 to filter out the AC in certain instances.

The dc or ac response current harmonic which provides the best spectral resolution is the one which should be selected for measurement. In the exemplary spectra shown in FIG. 2 the second harmonic of the ac response current provided the best resolution. For other plating baths or constituents, dc or different harmonics of the ac response current may provide better results. The in-phase component of the ac response current is then passed from in-phase output 18 of lock-in amplifier 6 to a display signal input 31 of system 7. Similarly, the quadrature component is passed from quadrature output 19 of lock-in amplifier 6 to a second display signal input 32 of system 7. The system 7 displays the in-phase and the quadrature components of the ac response current as a function of the dc sweep voltage of the total ac voltammetric signal. Since the dc sweep rate for a specific constituent is usually constant, the voltage axis also can be represented as a time axis. This display represents a unique ac response current spectra which is indicative of constituent concentration levels within the solution.

The dc response current is also displayed by system 7. Alternatively, a separate display means could be used for the dc response current signals. The separate display could be a strip-chart recorder, a computerized digital data acquisition system, an oscilloscope or other suitable display means. An exemplary dc response current display is shown in FIG. 3. The duration of the dc response current shown can provide an accurate indication of constituent concentration level.

The specific equipment used in the exemplary system of FIG. includes a Wavetek Model 188 waveform generator, a PAR 273 potentiostat and a PAR 5208 lock-in amplifier. The Wavetek waveform generator is available from Wavetek San Diego, Inc., of San Diego, Calif. and the PAR equipment is available from Princeton Applied Research, Princeton, N.J.

In order to optimize the accuracy of the ac and dc response current spectra produced in accordance with the exemplary ac and dc voltammetric techniques described above, it is necessary to vary a number of independent physical test parameters. For the ac voltammetric signals, these parameters include: 1) pretreatment signal amplitude and duration; 2) type of ac waveform (i.e., sinusoidal, square, triangular, etc.); 3) ac signal peak to peak amplitude and frequency; 4) dc sweep signal voltage range and sweep rate; 5) ac response current harmonic measured (i.e., first (or fundamental), second, etc.); and 6) ac response current phase angle measured.

In some cases the major constituent, for example, copper, in a Lea Ronal acid copper bath, is determined by a dc voltammetric signal which is simply the dc current resulting from the dc voltage sweep signal upon which the ac signal is superimposed. In this case, a slow dc sweep of 20 mv/sec starting from anodic potentials and sweeping into the plating range will yield a response current peak which is proportional to the copper ion concentration.

In general, the parameters which should be varied to optimize the spectral detail for the exemplary dc voltammetric signal include: 1) pretreatment signal amplitude and duration; 2) type of dc plating signal waveform; 3) plating signal amplitude and duration; 4) type of stripping signal waveform; 5) stripping signal amplitude and duration; and 6) signal response current characteristic measured.

The above ac and dc voltammetric system parameters were independently varied to determine the preferred system parameters for monitoring constituents in accordance with the present invention. It should be emphasized that the parameter range limits described below are average and that, the present invention may produce useful results with parameter values outside the specified ranges. In applying other voltammetric techniques in accordance with the method of the present invention, a similar set of parameters applicable to those techniques would have to be optimized. The set of applicable parameters may be estimated by reference to the manner in which the particular voltammetric technique has been applied to trace constituent detection.

In general, certain ranges of the above system parameters are particularly well-suited for monitoring major and trace constituent concentrations in accordance with the preferred embodiment of FIG. 1. All voltages are given with respect to a saturated calomel electrode. It is incidental that superimposed ac and dc are applied simultaneously. The desired dc or ac response current is culled from the combined waveforms. Therefore, the ranges given below apply to both the dc or ac methods. In terms of both the dc and ac voltammetric signals, the working electrode, usually a platinum wire about 1 mm in diameter and about 1 cm long, is preferably pretreated using a dc signal with an amplitude of about +1.5 to +3.5 volts and a duration of about 5 to 15 seconds. A sinusoidal ac waveform with an amplitude value set between 10 to 100 mv root mean square (rms) and a frequency set between about 30 to 20,000 Hz is superimposed on a dc sweep signal which is swept over an amplitude with a maximum range of about +1.0 to −2.5 volts and reversed to about −1.0 to +1.0 volts at a rate set between about 10 and 1,000 mv/sec. This sweep signal encompasses both stripping and plating electrode voltages. Optimal spectral peak resolution is obtained using the first or second harmonic of the ac response current, measured using a phase angle offset ranging between approximately 0 and 90 degrees. Numerous variations, including holds for brief periods at certain dc voltages, dc steps rather than sweeps to certain voltages, and several rather than just one sweep reversal may also be used.

Frequently, a trace constituent may produce a major perturbation of the dc response current over a significant range of dc potential. Then ac analysis is not required. For this reason, it is common, during the development of the best analytical procedures for a specific bath, to perform data analysis on all 3 types of spectra (i.e., dc, first harmonic, or second harmonic) obtained for a specific set of values of dc sweep with superimposed ac. For major constituents, the superposed ac may result in the best analytical procedure, or certain dc procedures which fall within the same approximate limits and conditions given above may be best. When dc voltages are held at a given value for brief periods, those holds can be set between about 100 msec and 10 seconds; and dc steps can be negative or positive between about 0.2 v and 3.5 volts. A solution flow rate of zero to about 500 ml/min past the sensing electrode wire is also an important variable for both dc and ac methods.

Each type of plating bath is unique and has a unique set of conditions for obtaining the optimum analysis, with the minimum interferences from other constituents.

An example of the optimization of the exemplary ac and dc voltammetric system of FIG. 1 to detection of specific plating bath constituents is as follows.

The method of the present invention was applied to the Lea Ronal Corp. Kadizid acid cadmium plating bath available from Lea Ronal Corporation of Freeport, N.Y. This plating bath contained multiple organic addition agents, including Starter K (a Lea Ronal proprietary composition comprising ethoxylated surfactants), Brightener KR (a Lea Ronal proprietary composition to brighten the deposit), Stabilizer (a Lea Ronal proprietary composition comprising alkyl-aryl thiourea derivatives including N,N'-diethyl-thiourea), and wetting agent K13 (a Lea Ronal proprietary composition). In addition to the four trace addition agents, analysis for trace levels of copper contamination was obtained, and analysis for cadmium and sulfuric acid, the two major constituents, was obtained. DC, first harmonic and second harmonic ac methods were compared for all seven constituents. The best diagnostic spectra with the least interference from other constituents were chosen.

In each case, a pretreatment voltage of +3.0 v for 10 seconds was used on a 1.0 mm diameter platinum wire, with the last 1.3 cm length exposed to the plating bath. After the pretreatment, a step was taken from +3.0 V to whatever voltage is first listed in each procedure below. The procedures are as follows:

Procedure 1: Starter K a) DC method, with holds
b) DC hold: 100 msec at −2.0 volts
c) Step to +0.5 volts
d) DC hold: 1 second at +0.5 volts
e) Zero solution flow.

Procedure 2: Stabilizer a) DC method, with sweeps
b) Sweep at 50 mv/sec from −1.1 V to −1.35 V to −0.5 V to −1.35 V to −0.5 V.
c) Zero solution flow.

Procedure 3: Brightener KR a) DC method, with sweep
b) Sweep at 50 mv/sec −1.1 V to −1.35 V to −0.5 V
c) Flow continuous during pretreatment and sweep at about 250 ml/minute.

Procedure 4. Wetting agent K13 a) Second harmonic AC method, with holds and sweep
b) 400 Hz, 25 mv rms, 65° reference phase angle
c) DC hold: 10 seconds at −1.35 V
d) Step to +0.5 V
e) DC hold: 100 msec at 0.5 V
f) Step to −0.5 V
g) Sweep at 50 mv/sec from −0.5 V to −1.35 V to −0.5 V
h) Flow continuous at about 250 ml/minute.

Procedure 5: Copper contaminant a) DC method, with sweeps
b) Sweep at 50 mv/sec from 0 V to −1.35 V to −0.5 V to −1.35 V to −0.5 V
c) Flow continuous at about 250 ml/minute.

Procedure 6: Cadmium a) DC method, with holds
b) DC hold: −2.0 volts at 1 second
c) Step to +0.5 V
d) DC hold: 600 msec
e) Zero solution flow.

Procedure 7: Sulfuric acid a) First Harmonic ac method, with hold
b) DC hold: 10 seconds at 0 V
c) 10,000 Hz at 25 mv rms, 90° reference phase angle
d) Zero solution flow.

The method has also been applied to an exemplary chromium plating bath. The ac voltammetric techniques were used to detect the concentration levels of chromium ions and silicofluoride ions, while the dc techniques provided maximum spectral detail for determining sulfate ion concentration. The method will provide similar improvements in voltammetric measurement accuracy for many other types of plating baths.

Although the foregoing description has described the use of exemplary ac and dc voltammetric techniques, this is by way of example and not limitation. Many other ac and dc signals and techniques could be used to provide similar advantages. It will be understood by those skilled in the art that these and many other alternate implementations are possible without deviating from the scope of the invention, which is limited only by the appended claims.

What is claimed is:

1. A method for monitoring constituent concentration in a plating bath solution containing a plurality of constituents, said method comprising the steps of:
   (a) applying a pretreatment signal having an amplitude of about $+1.5$ V to $+3.5$ V and duration of about 5 seconds to about 15 seconds to a working electrode positioned within said solution to form a pretreated electrode;
   (b) pumping said plating bath solution past said working electrode at a solution flow rate;
   (c) applying an ac voltammetric signal to said pretreated electrode, wherein said ac voltammetric signal is a constant amplitude ac signal superimposed on a sweep signal, said ac signal having a peak to peak amplitude of about 10 to 100 millivolts rms and a frequency of about 30 to 20,000 Hz and said sweep signal having a dc voltage range of about $+1.0$ to $-2.5$ volts and a sweep rate of about 10 to 10,000 mv/sec, said ac voltammetric signal producing an ac response current;
   (d) measuring said ac response current at one or more phase angles with respect to said ac voltammetric signal wherein measuring said ac response current involves the steps of varying in combination each parameter comprising said peak to peak amplitude of said ac signal, said frequency of said ac signal, said sweep rate of said sweep signal, said dc voltage range of said sweep signal, said one or more phase angles, and said amplitude and duration of said pretreatment signal, to determine the specific value of each parameter which, when taken in combination with the remaining said parameters, provides maximum spectra detail and minimum interferences from other constituents;
   (e) applying said pretreatment signal to said working electrode positioned within said solution to form a pretreated electrode;
   (f) applying a dc voltammetric signal to said pretreated electrode, said dc voltammetric signal producing a dc response current;
   (g) measuring said dc response current;
   (h) comparing the relative detail of said ac and said dc response current spectra for the selective and sensitive detection of particular constituents within said solution;
   (i) using said ac response current spectra to monitor the concentration of those particular constituents for which said ac spectra provide maximum spectral detail with minimum interference from other constituents; and
   (j) using said dc response current spectra to monitor the concentration of those particular constituents for which said dc spectra provide maximum spectral detail with minimum interferences from other constituents.

2. The method of claim 1 wherein said dc sweep signal is set to have one or more dc holds within the range of about 100 milliseconds to 10 seconds.

3. The method of claim 2 wherein said dc sweep signal is set to vary in steps in a positive or negative voltage direction wherein said steps have a value within the range of about 0.2 volts to 3.5 volts.

4. The method of claim 1 wherein said dc sweep signal is set to vary in steps in a positive or negative voltage direction wherein said steps have a value within the range of about 0.2 volts to 3.5 volts.

5. The method of claim 1 wherein said measuring of said ac response current is made at the first or second harmonic frequency of said constant amplitude ac signal so as to further maximize said ac spectra detail.

6. The method of claim 1 wherein said solution flow rate is within the range of zero to about 500 ml per minute.

7. The method of claim 1 wherein said plating bath is an acid cadmium plating bath containing several organic addition agents, and wherein the concentration level of at least one of said organic addition agents is determined using said ac response current spectra and the concentration level of at least one other said organic addition agent is determined using said dc response current spectra.

8. The method of claim 1 wherein said plating bath is a chromium plating bath containing sulfate ions, chromium ions and silicofluoride ions, and wherein the concentration level of said sulfate ions is determined using said dc current spectra and the concentration level of said chromium ions and said silicofluoride ions is determined using said ac current spectra.

* * * * *